(12) United States Patent
Molchanov et al.

(10) Patent No.: US 11,819,601 B2
(45) Date of Patent: Nov. 21, 2023

(54) BONE DUST TRAP

(71) Applicants: Ruslan Molchanov, Calgary (CA); Irina Molchanova, Calgary (CA)

(72) Inventors: Ruslan Molchanov, Calgary (CA); Irina Molchanova, Calgary (CA)

(*) Notice: Subject to any disclaimer, the term of this patent is extended or adjusted under 35 U.S.C. 154(b) by 291 days.

(21) Appl. No.: 17/058,687

(22) PCT Filed: Sep. 17, 2018

(86) PCT No.: PCT/CA2018/051149
§ 371 (c)(1),
(2) Date: Nov. 25, 2020

(87) PCT Pub. No.: WO2018/227311
PCT Pub. Date: Dec. 20, 2018

(65) Prior Publication Data
US 2021/0402079 A1    Dec. 30, 2021

(30) Foreign Application Priority Data

Jul. 30, 2018   (CA) .................................. CA 3012795

(51) Int. Cl.
*A61M 1/00* (2006.01)
*A61B 17/16* (2006.01)

(52) U.S. Cl.
CPC .............. *A61M 1/631* (2021.05); *A61M 1/88* (2021.05); *A61B 17/16* (2013.01); *A61B 2217/005* (2013.01); *A61M 2205/7545* (2013.01); *A61M 2206/16* (2013.01); *A61M 2206/20* (2013.01); *A61M 2210/02* (2013.01)

(58) Field of Classification Search
CPC ...... A61M 1/79; A61M 2210/02; A61M 1/88; A61M 1/631; A61M 2205/7545; A61M 2206/16; A61M 2206/20; A61B 17/16; A61B 2217/005
See application file for complete search history.

(56) References Cited

U.S. PATENT DOCUMENTS

| | | | |
|---|---|---|---|
| 3,785,380 A | | 1/1974 | Brumfield |
| 4,385,891 A | * | 5/1983 | Ligotti ................ A61C 17/065 433/92 |
| 4,439,319 A | * | 3/1984 | Rock ...................... B01D 35/30 210/489 |

(Continued)

*Primary Examiner* — Susan S Su
*Assistant Examiner* — Ted Yang

(57) ABSTRACT

The Bone Dust Trap for collecting bone dust during various surgical procedures for subsequent bone graft implantation. The device includes cylindrical housing unit covered with the lid, attached to the central pipe with the porous tip. The pipe connects the cyclone forming mechanism and filtrating membrane, located at the lower part of the central pipe. The membrane interlinks with the plurality of porous plates located along the walls of the cylinder. The cyclone forming mechanism, consisting of the inlet port with conical jet and the spiral helix, creates spiral movement of the incoming fluid. The liquid is further directed towards the 2-stage filtrating system with the said porous plates, where larger bone particles are accumulated, and then to the filtrating membrane, which collects smaller particles. The fluid is extracted through the central pipe. The lid can be removed to collect the bone particles from plates and membrane.

10 Claims, 5 Drawing Sheets

(56) References Cited

U.S. PATENT DOCUMENTS

| | | | |
|---|---|---|---|
| 4,643,197 A * | 2/1987 | Greene | A61M 1/79 604/319 |
| 4,850,964 A * | 7/1989 | Cotter | A61M 1/79 604/319 |
| 5,290,445 A * | 3/1994 | Buttery | B29C 66/54 156/218 |
| 5,624,418 A * | 4/1997 | Shepard | A61M 1/79 210/85 |
| 5,630,939 A * | 5/1997 | Bulard | B01D 35/02 433/92 |
| 5,766,134 A * | 6/1998 | Lisak | A61B 10/025 604/320 |
| 5,779,649 A * | 7/1998 | Herbert | A61M 1/79 604/319 |
| 5,954,961 A | 9/1999 | Carchidi | |
| 6,099,493 A * | 8/2000 | Swisher | A61M 1/631 604/4.01 |
| 6,299,763 B1 * | 10/2001 | Ashman | B01D 46/24 210/450 |
| 6,387,070 B1 | 5/2002 | Marino et al. | |
| 6,872,184 B2 | 3/2005 | Brannon | |
| 7,204,810 B2 | 4/2007 | Hynes et al. | |
| 7,758,556 B2 | 7/2010 | Perez-Cruet et al. | |
| 7,951,089 B2 | 5/2011 | Miller | |
| 7,971,728 B2 | 7/2011 | Anspach et al. | |
| 8,465,439 B2 * | 6/2013 | Parks | A61M 1/60 604/319 |
| 8,740,908 B2 * | 6/2014 | Farley | A61F 2/4644 606/86 R |
| 8,845,605 B2 | 9/2014 | Hensler et al. | |
| 9,089,801 B1 * | 7/2015 | Gavlak | A61M 1/79 |
| 9,220,485 B2 * | 12/2015 | Parks | A61B 10/0045 |
| D771,832 S * | 11/2016 | Yeager | D24/224 |
| 9,872,944 B1 * | 1/2018 | Willard | A61B 10/0045 |
| 2002/0026212 A1 * | 2/2002 | Wholey | A61M 1/79 606/191 |
| 2003/0130594 A1 * | 7/2003 | Hynes | A61M 1/79 600/562 |
| 2004/0115590 A1 * | 6/2004 | Takahashi | A61C 17/065 433/92 |
| 2005/0139532 A1 * | 6/2005 | Hershberger | B01D 35/153 210/136 |
| 2005/0189288 A1 * | 9/2005 | Hershberger | B09B 3/0075 210/473 |
| 2006/0005276 A1 | 3/2006 | Falco et al. | |
| 2006/0052760 A1 * | 3/2006 | Batzdorf | A61M 1/79 604/319 |
| 2007/0203471 A1 * | 8/2007 | Anspach | A61M 1/3692 604/406 |
| 2007/0225665 A1 * | 9/2007 | Perez-Cruet | A61M 1/79 604/317 |
| 2008/0243029 A1 * | 10/2008 | Howard | A61M 1/79 600/565 |
| 2009/0306669 A1 * | 12/2009 | Takahashi | A61C 17/08 606/80 |
| 2012/0111778 A1 * | 5/2012 | Gavlak | A61M 1/602 210/406 |
| 2012/0330220 A1 * | 12/2012 | Hensler | A61M 1/60 604/319 |
| 2014/0121560 A1 * | 5/2014 | Parks | A61B 10/02 600/562 |
| 2016/0262774 A1 * | 9/2016 | Honda | A61M 1/79 |
| 2016/0325018 A1 * | 11/2016 | Assell | A61M 1/79 |
| 2017/0224887 A1 * | 8/2017 | Minskoff | B01D 19/0057 |
| 2017/0348468 A1 * | 12/2017 | Kana | A61M 1/79 |
| 2018/0043068 A1 * | 2/2018 | Willard | A61B 10/0045 |

* cited by examiner

BONE DUST TRAP

TECHNICAL FIELD

This invention relates to bone particles collecting devices used for separating of bone fragments from various substances, such as blood, irrigation fluids, tissue particles and other fluids, extracted from the patient during surgical procedure; and particularly devices for retaining and collecting bone fragments from extracted fluid. The Bone Dust Trap includes a unique 2-stage filtration system allowing to collect large number of bone particles including smallest units.

The invention possesses numerous benefits and advantages over known bone particles collecting devices, addressing the following issues:

1. Existing devices are based on one-stage filtration system with the certain size of the pores. The one-stage filtration system separates only bone particles of the certain size. If the pores are quite large, it leads to washing out of the smaller bone dust, which prevents collecting it for future implantation. If the size of the pores is too small, they are quite often get clogged.

The Bone Dust Trap is designed to collect the most possible amount of the bone particles preventing excessive washing out due to highly efficient 2-stage filtration system. The first stage consists of the plurality of plates, with larger pores, located vertically on the inner surface of the cylindrical housing unit. The larger bone particles are accumulated on the above mentioned plates during the filtration process.

The second stage of the 2-stage filtration system is a circular pours membrane with smaller pores, located on the lower part of the central pipe in the cylindrical housing unit. The membrane collects the smallest bone particles.

Another unique feature of the Bone Dust Trap is the option to clean the bone particles from blood by sucking the irrigation liquid in, and then extracting it again through the central pipe. The 2-stage filtration system prevents washing out of the bone particles during the cleaning process.

2. Common drawback of the most of the existing bone particles collecting devices is inefficient design, where inlet and outlet tubes are located on the opposite sides, which makes the devices to large to be placed into the drape pouch for stable positioning. Some of the collecting devices are fixed to the drape covering patient during the procedure, with a clip. Such fixation does not provide stable positioning. During surgical procedure, once the position of the device is altered, the device may stop functioning properly. Under certain angles of positioning, the known devices are not able to collect bone particles at all, therefore fewer bone particles are collected overall during the procedure.

The other group of known devices can fit into the drape pouch, however, they are too small in size, and therefore are hard to be found and removed from the pouch during the procedure, which makes the procedure more time consuming and less efficient due to additional distraction of the surgeon.

Design of the Bone Dust Trap is highly efficient and ensures stable positioning. The inlet and outlet tubes are located on the same side of the Bone Dust Trap, which allows the device to be placed into the drape pouch for secure stable positioning. The size of the Bone Dust Trap allows it to perfectly fit into the pouch of the drape and to be easily removed from the drape.

3. The other existing bone particles collecting devices are quite small in size and require to be emptied frequently, which makes the surgical procedure more time consuming and thus less cost efficient.

The Bone Dust Trap measurements are 40 mm in diameter, which is 2 or more times larger than the size of existing devices and allows it to fit the drape pouch perfectly.

4. One more advantage of the Dust Trap is durability. The existing devices are known to have easily breakable fragile inlet and outlet tubes.

The Bone Dust Trap inlet and outlet tubes' walls are 2.5 times thicker than those of existing similar devises, which provides durability and cost efficiency.

5. The other unique feature of the Bone Dust Trap ensures perfect tightness of the device. The outlet port of the Bone Dust Trap is shaped conically to provide rigid connection with the standard suction tubing. The outlet port inner diameter on the outlet side is larger than the inner diameter of the inlet port on the inlet side. Different in size inner diameters the said outlet and inlet port create negative pressure to ensure tightness of the device.

BACKGROUND ART

The bone collecting devices have been known and used in spinal, orthopedic and dental surgeries. The known devices can be divided in two main groups. The first group includes devices that are usually placed outside operative field, in a non sterile zone. The second group includes devices placed inside operative field, in a sterile zone. The second group can be sub-divided into several types of bone particles collecting devices: (1) connected directly to the drill, (2) connected to suction tip directly. (3) connected to suction tip through the flexible line. The Bone Dust Trap belongs to the third type of the second group. The bone collecting devices of this type are represented in the following patents:

| | |
|---|---|
| US006022354A | Mercury |
| U.S. Pat. No. 7,951,089B2 | Miller |
| U.S. Pat. No. 3,785,380A | Brumfield |
| U.S. Pat. No. 5,766,134A | Lisak, Young |
| U.S. Pat. No. 7,204,810B2 | Hynes, Strong |
| U.S. Pat. No. 7,971,728B2 | Anspach, Bucina |
| U.S. Pat. No. 7,758,556B2 | Perez-Cruet, Pepper, Miller |

Though such bone collecting devices are currently used in the industry, there has being a need for 75 considerable improvement.

DISCLOSURE OF INVENTION

The Bone Dust Trap is a filtration device for collecting bone dust and particles during various surgical procedures for subsequent bone graft implantation. The device includes cylindrical housing unit with plurality of porous plates placed along the inner surface. The cylindrical housing unit is covered with the lid, attached to the central pipe. The opposite end of the central pipe has porous tip. The central pipe connects the cyclone forming mechanism with the filtrating membrane, located at the lower end of the central pipe above the porous tip. The membrane contains slots to interlink with the said porous plates. The porous plates fit into the slots of the membrane, which allows membrane to scrap bone particles from the plates. The cyclone forming mechanism includes the inlet port with conical jet and the spiral helix. The cyclone forming mechanism creates spiral movement of the incoming liquid. The liquid is further directed towards the 2-stage filtration system. The first stage of the 2-stage filtration system includes the above mentioned porous plates to accumulate larger bone particles.

The second stage is a filtration membrane with smaller pores for collecting smaller bone particles.

The bone particles are separated and accumulate on the plates and membrane surfaces. The suction line is connected to the outlet to extract the remaining fluid through the central pipe. The fluid is sucked into the central pipe through the porous tip at the end of the pipe located under the membrane. The lid of the cylinder is removed to collect the bone particles. While the lid is being removed, the central filtrating membrane scraps the bone particles from the porous plates.

The Bone Dust Trap can additionally be used in dental industry. The size of the device can be adjusted to fit the needs of dental surgeons.

MODES FOR CARRYING OUT THE INVENTION

Figure 1:
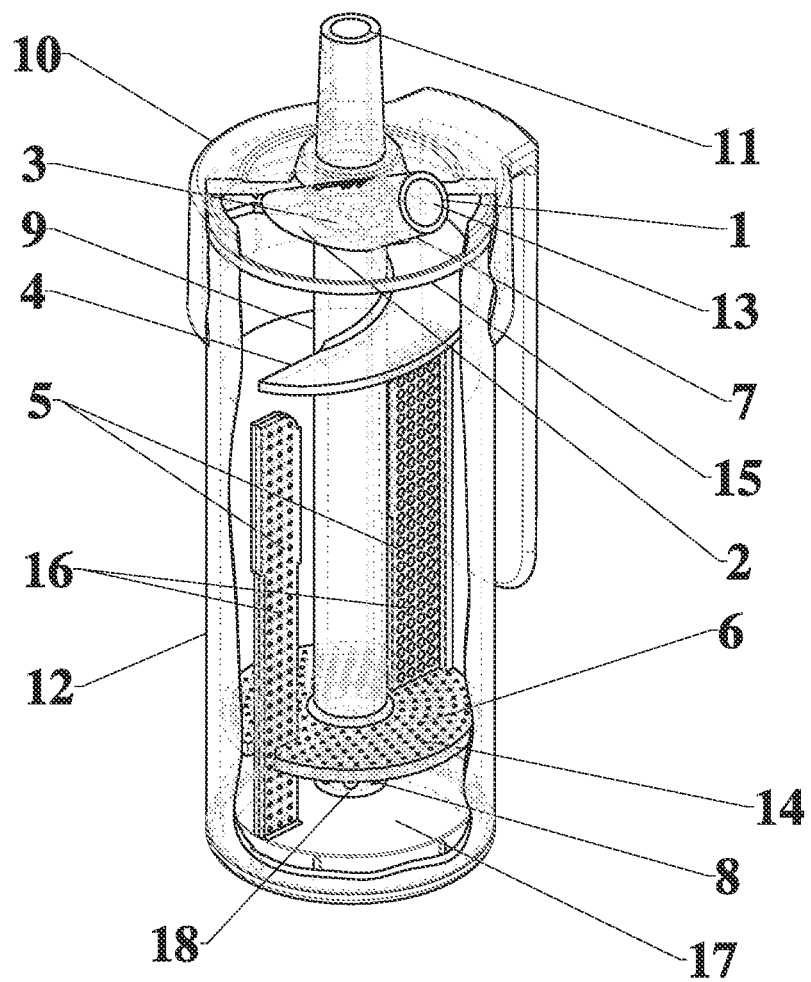
FIG. 1 is a perspective view of the Bone Dust Trap in a assembled state.
Figure 2:
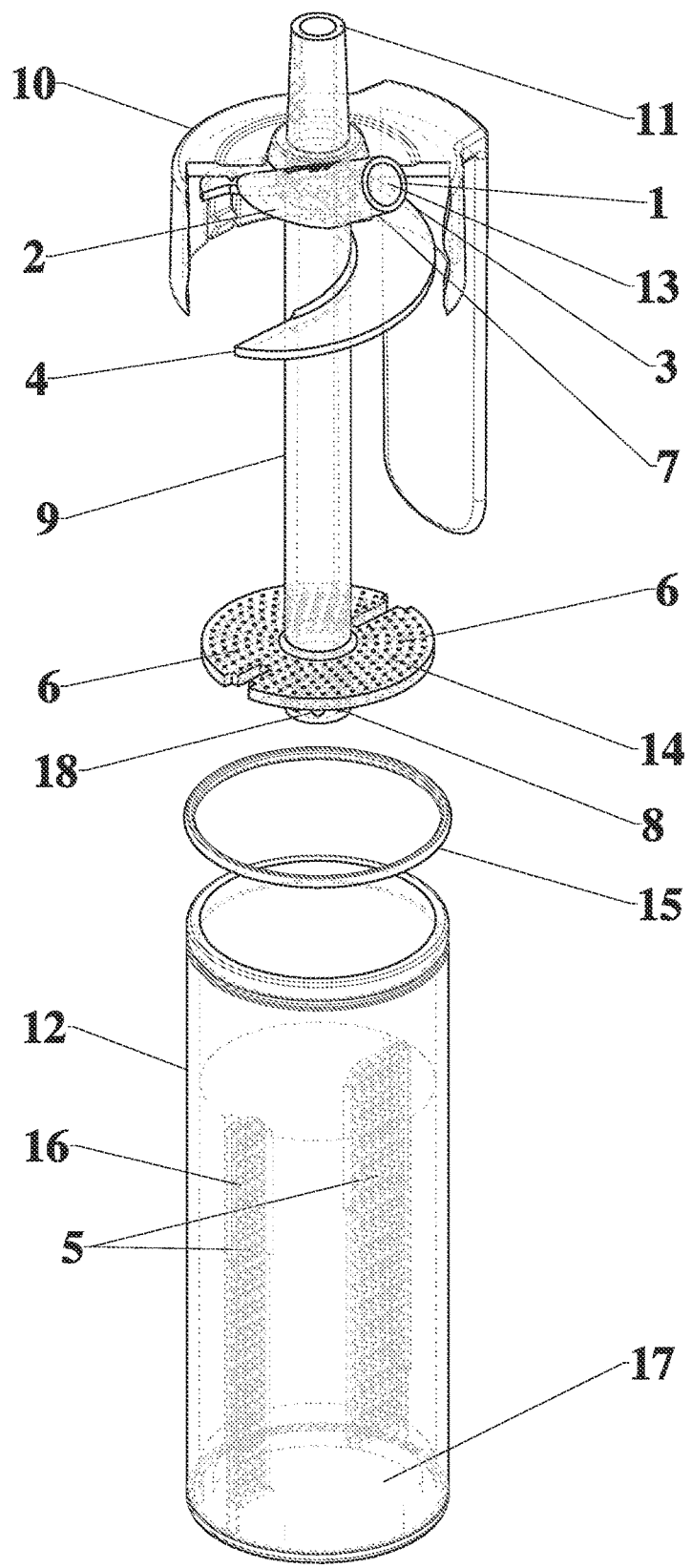
FIG. 2 is a perspective view of the Bone Dust Trap in a partially disassembled state.
Figure 3:
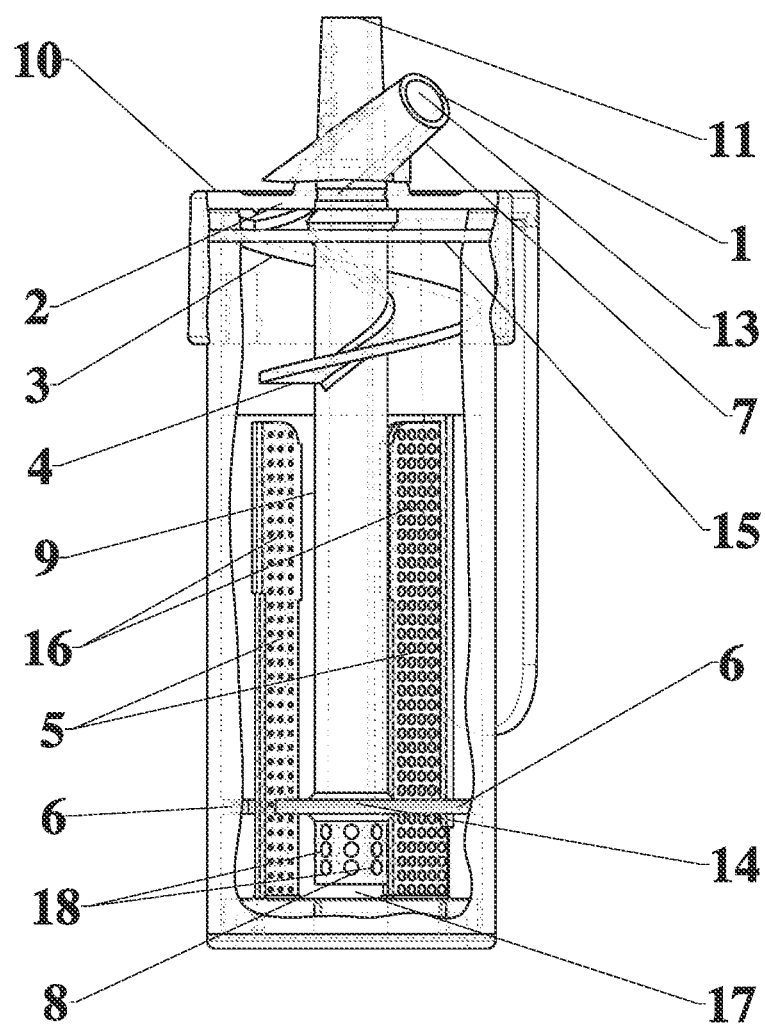
FIG. 3 is a side cross-sectional view of the upper part of the invention including the lid and the spiral helix.
Figure 4:
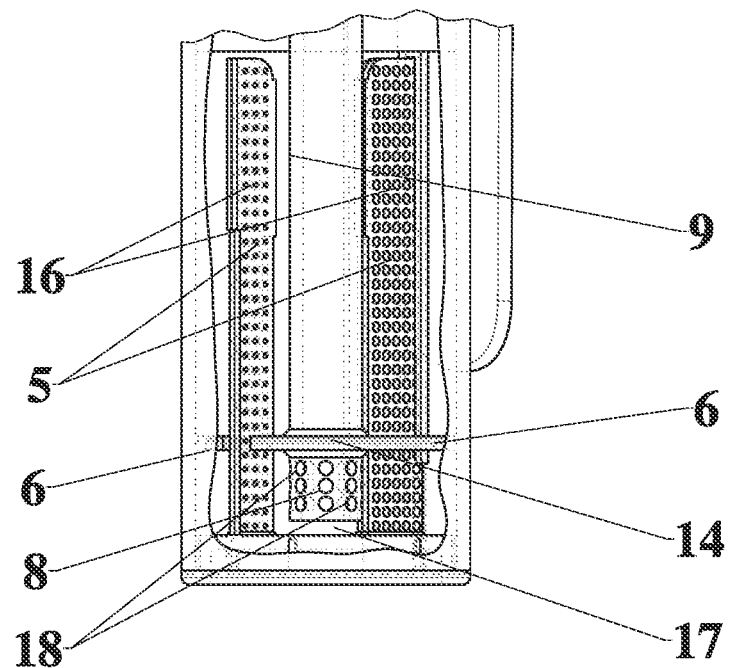
FIG. 4 is a side cross-sectional view of the lower part of the invention including the housing cylindrical unit, central pipe with the porous tip, filtrating plates and central filtrating membrane.
Figure 5:
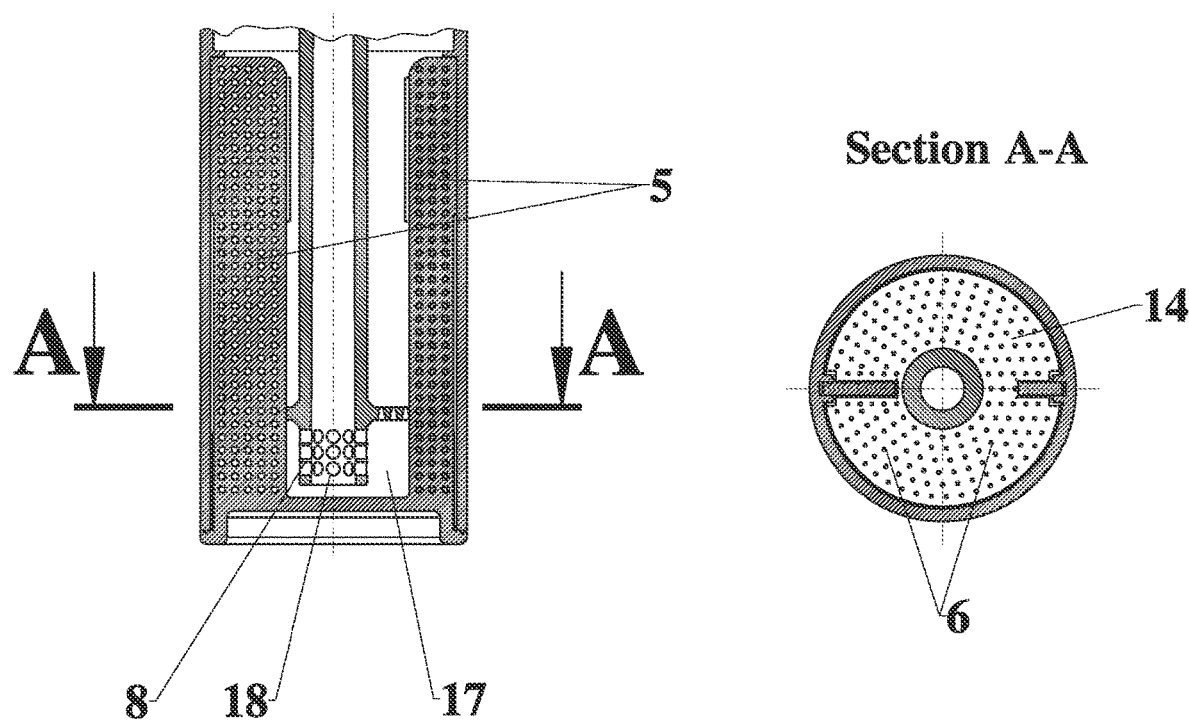
FIG. 5 is a side cross-sectional view of the lower part of the invention.

With reference to the drawings and, in particular, with reference to FIGS. 1-5, the Bone Dust Trap consists of the two main parts: the cylindrical housing unit, indicated generally at 12, fabricated of a plastic material, preferably transparent; and the lid—10 with the built in cyclone forming system, comprising of the spiral helix—3-4 and inlet port—1.

The fluids incoming from the patient are delivered into the Bone Dust Trap through the inlet port—1, comprising of the cylindrical tube—13 with conical jet—2. The inlet port connects to the suction line through the conical jet to direct fluids towards the spiral helix—3-4. The spiral helix is attached to the lid—10 and wrapped around the central pipe—9.

The outer surface of the said inlet port is conically shaped—7 to provide tight connection with the flexible suction line delivering fluids from the patient during the surgical procedure.

The incoming fluids are then directed towards the upper end of the spiral helix—3 and forming cyclonic motion, move towards the lower end of the spiral helix—4. The distal part (lower end) of the spiral helix—4 is ending at the level of the filtrating porous plates—5, located along the inner sides of the cylindrical housing unit. Leaving the spiral helix, the fluid is directed towards the filtrating plates with plurality of pores—16, where larger bone particles are accumulated. Smaller bone particles—bone dust, which pass through the porous plates are further accumulated on the smaller pores of the central filtrating membrane—14.

The combination of porous plates and central filtrating membrane are forming the 2-stage filtrating system, allowing to accumulate larger number of the bone particles.

The membrane is rigidly connected to the central pipe and additionally includes plurality of slots—6 peripherally located corresponding to the location and size of the filtrating plates. When the lid with the connected central pipe and membrane is pulled out, the membrane slots scrub the bone particles from the porous plates surface. The membrane peripheral surface also mechanically collects the bone dust and particles accumulated on the inner surface of the cylindrical housing unit. The filtrated fluid passing through the central filtrating membrane is directed into the lower receptacle—17. From there, the fluid is delivered into the central pipe through the porous tip—8 of the central pipe. The porous tip includes plurality of pores—18 to prevent clogging from blood clots.

Directed through the central pipe, the fluid is eventually extracted from the device through the conically shaped outlet port—11.

The outlet port inner diameter on the outlet side is larger than the inner diameter of the inlet port on the inlet side to create negative pressure and ensure tightness of the device.

The lid of the Bone Dust Trap is tightly connected to the housing unit through the o-ring—15.

What is claimed is:

1. A Bone Dust Trap for collecting bone particles from a patient during surgical procedure comprising of:
    a cylindrical housing unit having a plurality of porous filtrating plates located along inner walls of the said cylindrical housing unit;
    a lid;
    an o-ring ensuring tightness of the Bone Dust Trap when the Bone Dust Trap is sealed;
    a cyclone forming mechanism, comprising of a spiral helix and a cylindrical tube with conical jet forming an inlet port;
    a central pipe with a porous tip for extraction of filtrated fluids;
    a multi-stage filtrating system, comprising of the plurality of porous filtrating plates and a central filtrating membrane, wherein the said central filtrating membrane is rigidly attached to the said central pipe wherein the said central filtrating membrane includes a plurality of pores for filtrating bone dust and a plurality of slots to interlink with the said plurality of porous filtrating plates, wherein the plurality of slots allows to scrap bone particles from the said plurality of porous filtrating plates as the lid is removed;
    the porous tip with a plurality of pores, located at an end of the said central pipe under the central filtrating membrane;
    the inlet port and an outlet port attached to the said lid and shaped conically in order to provide rigid connection to a suction line and a suction tubing respectively.

2. The Bone Dust Trap defined in claim 1 wherein the said inlet port is connected to the suction line and directs incoming fluid from the patient towards the spiral helix, attached to the lid and wrapped around the central pipe, wherein a distal part of the said spiral helix is reaching a level of the plurality of porous filtrating plates.

3. The Bone Dust Trap according to claim 1 includes the said cyclone forming mechanism, comprising of the said inlet port wherein the said inlet port is positioned at an angle of between 0 to 90 degrees to a longitudinal axis of the Bone Dust Trap and the spiral helix.

4. The Bone Dust Trap according to claim 1 includes the said multi-stage filtrating system comprising of the said central filtrating membrane and the plurality of porous filtrating plates with plurality of pores for accumulating larger bone particles, whereas the said porous filtrating plates are located along the inner walls of the cylindrical housing unit.

5. The Bone Dust Trap according to claim 1 additionally includes the central pipe for extraction of filtrated fluids, wherein an upper end of the said central pipe is attached to the said lid, and a lower end of the said central pipe ends with the porous tip with the plurality of pores to prevent clogging from blood clots.

6. The Bone Dust Trap according to claim 1, wherein a size of the pores of the said central filtrating membrane is smaller than a size of the pores of the plurality of porous filtrating plates.

7. The Bone Dust Trap according to claim 1 wherein the said central filtrating membrane is comprising of the plurality of the slots, allowing the porous filtrating plates to pass through the central filtrating membrane as the lid is pulled when being removed; wherein the central filtrating membrane comprises a peripheral surface that mechanically collects the bone dust and particles accumulated on an inner surface of the said cylindrical housing unit.

8. The Bone Dust Trap according to claim 1 consists of a combination of the cyclone forming mechanism with the said multi-stage filtrating system.

9. The Bone Dust Trap according to claim 1 wherein an outlet port inner diameter is larger than an inner diameter of the inlet port in order to create negative pressure to ensure tightness of the Bone Dust Trap; wherein the said inlet port and outlet port are shaped conically.

10. The Bone Dust Trap according to claim 1 additionally includes the said o-ring positioned at a junction of the lid and the cylindrical housing unit to tightly seal the Bone Dust Trap.

* * * * *